United States Patent
Iwata et al.

[11] Patent Number: 5,885,981
[45] Date of Patent: *Mar. 23, 1999

[54] ANTIBACTERIAL PENEM ESTERS DERIVATIVES

[75] Inventors: Hiromitsu Iwata, Takatsuki; Takashi Nakatsuka, Mishima-gun; Rie Tanaka, Ibaraki; Masaji Ishiguro, Takarazuka, all of Japan

[73] Assignee: Suntory Limited, Osaka, Japan

[*] Notice: The term of this patent shall not extend beyond the expiration date of Pat. No. 5,830,889.

[21] Appl. No.: 470,944

[22] Filed: Jun. 6, 1995

Related U.S. Application Data

[63] Continuation of Ser. No. 971,829, filed as PCT/JP91/01098, Aug. 16, 1991.

[30] Foreign Application Priority Data

Aug. 20, 1990  [JP]  Japan ................................. 2-217052

[51] Int. Cl.$^6$ ......................... C07D 477/06; A61K 31/43
[52] U.S. Cl. ................................ 514/195; 540/310
[58] Field of Search ............................. 540/310; 514/195

[56] References Cited

U.S. PATENT DOCUMENTS

| | | | |
|---|---|---|---|
| 4,479,947 | 10/1984 | Christensen et al. | 540/310 |
| 4,997,829 | 3/1991 | Ishiguro et al. | 540/310 |
| 5,036,063 | 7/1991 | Lattrell et al. | 540/310 |

*Primary Examiner*—John M. Ford
*Attorney, Agent, or Firm*—Oblon, Spivak, McClelland, Maier & Neustadt, P.C.

[57] ABSTRACT

Antibiotic penem compounds are represented by the following formula:

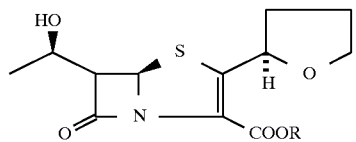

wherein R represents a group of the general formula:

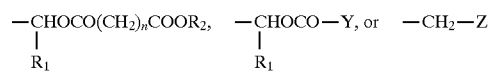

in which $R_1$ is a hydrogen atom or linear or branched $C_1$—$C_6$ alkyl group, $R_2$ is a particular substituted or unsubstituted alkyl, aryl or aralkyl group, n is an integer of 1–6, Y is a 5- or 6-membered heterocyclic aliphatic group having 1 or 2 oxygen atoms in the ring thereof, and Z is a specific 5-substituted 2-oxo-1,3-dioxolen-4-yl group. Antibiotic compositions for oral administration are also described.

7 Claims, No Drawings

ANTIBACTERIAL PENEM ESTERS DERIVATIVES

This is a Continuation of application Ser. No. 07/971,829, filed on Feb. 19, 1993, pending, which was filed as International Application No. PCT/JP91/01098, filed Aug. 16, 1991.

TECHNICAL FIELD

The present invention relates to penem compounds, and more specifically to penem compounds which are expected to find clinical utility as promising antibiotics.

BACKGROUND ART

The present inventors previously found that a group of penem compounds represented by the following formula (V):

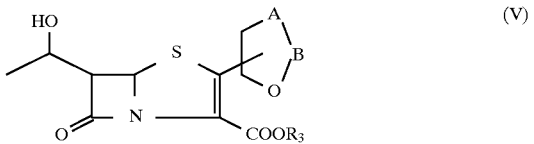

wherein $R_3$ is a hydrogen atom or allyl group, —A— represents an oxygen or methylene group, and —B— represents a methylene, ethylene or carbonyl group, and their salts have excellent antibacterial activities on both gram-positive and gram-negative, aerobic or anaerobic bacteria (Japanese Patent Laid-Open No. 207387/1986).

High safety of these compounds has been confirmed by a safety test in which laboratory animals were used. Their development as medical drugs is now expected.

In the meantime, it has been found by the study on the correlation between structure and antibacterial activities of these compounds [J. Antibiotics, 41, 1685 (1988)] that, among 2-substituents of penem, (R)-2-tetrahydrofuryl group provides the highest antibacterial activities while (S)-2-tetrahydrofuryl group, a diastereomer at its 2-side chain group, and (R) or (s)-3-tetrahydrofuryl group, a position isomer, provide weaker activities particularly against gram-negative bacteria.

From these reasons, compounds represented by the following formula (VI):

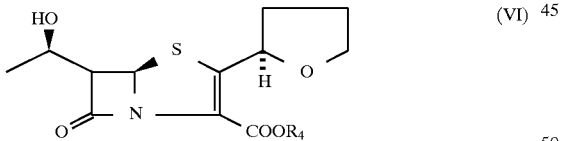

wherein $R_4$ represents a hydrogen atom or a group capable of forming a pharmaceutically-acceptable salt, have drawn interests as antibiotics. These compounds are also interested in that they do not require any special chemical modification for oral absorption and they themselves can be developed as both injections and oral drugs.

The bioavailability of the above-described compounds per se in laboratory animal (rats) has been found by no means inferior to commercial drugs which are used clinically.

However, from the viewpoint of safety and economy, further enhancement of their bioavailability upon oral administration is apparently more advantageous. As far as the above compounds are concerned, there is yet room for further improvement in this regard.

Regarding improvements on the absorption upon oral administration, active studies have been conducted on penicillin and cephalosporin antibiotics so that many of these antibiotics are used as curative medicines. There are, however, only a few study reports of this type on penem and carbapenem antibiotics [J. Antibiotics, 36, 983, (1983); Japanese Patent publication No. 67287/1990]. It has therefore been interest in determining whether or not the approaches used for penicillin and cephalosporin antibiotics are equally applicable to penem compounds.

DISCLOSURE OF INVENTION

The present inventors have carried out an extensive investigation on the compounds (VI) with a view toward making an improvement in their bioavailability. As a result, it has been found that protection of their carboxyl group with a particular ester-forming group can significantly improve their bioavailability, leading to the completion of the present invention.

The present invention provides a penem compound represented by the following formula (I):

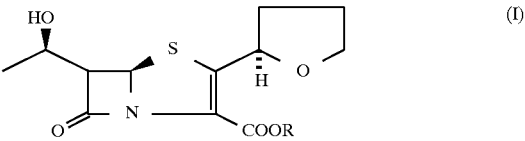

wherein R represents a group of the general formula (II), (III) or (IV):

in which $R_1$ is a hydrogen atom or a linear or branched $C_1$—$C_6$ alkyl group; $R_2$ is a $C_1$—$C_6$ alkyl or alkenyl group, a $C_6$—$C_{10}$ aryl group, a $C_7$—$C_{11}$ aralkyl group, or a said $R_2$ each group substituted by one or more substituents selected from $C_1$—$C_6$ alkyl groups, $C_6$—$C_{10}$ aryl groups, $C_7$—$C_{11}$ aralkyl groups, hydroxyl groups, $C_1$—$C_6$ alkoxyl groups and/or halogen atoms; and n is an integer of 1–6,

in which $R_1$ has the same meaning as defined above; Y is a 5- or 6-membered heterocyclic aliphatic group having 1 or 2 oxygen atoms in the ring thereof, or

in which Z is a 5-substituted 2-oxo-1,3-dioxolen-4-yl group, said 5-substituent being a $C_1$—$C_6$ alkyl group, a $C_6$—$C_{10}$ aryl group, a $C_7$—$C_{11}$ aralkyl group, or a said 5-substituent substituted by one or more substituents selected from $C_1$—$C_6$ alkyl groups, $C_6$—$C_{10}$ aryl groups, $C_7$—$C_{11}$ aralkyl groups, hydroxyl groups, $C_1$—$C_6$ alkoxyl groups and halogen atoms.

BEST MODE FOR CARRYING OUT THE INVENTION

The penem compound (I) of the present invention can be synthesized, for example, by reacting a halogenated alkyl compound (VII) with a penem compound (VI') in accordance with the following formula:

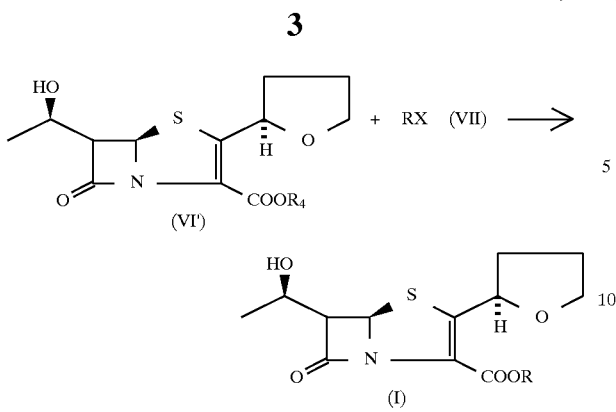

wherein X represents a halogen atom, $R_4$ represents a hydrogen or alkali metal atom or an amino residuum, and R has the same meaning as defined above.

When $R_4$ in the compound (IV') is an alkali metal atom or an amino residuum in this invention, the target compound can be obtained by stirring the compound (VI') and the halogenated alkyl compound (VII) in an organic solvent.

When $R_4$ in the compound (VI') is a hydrogen atom, on the other hand, it is firstly reacted with an alkali metal hydroxide, an alkali metal salt or an amine compound in an organic solvent to form a salt. The halogenated alkyl compound (VII) is then reacted with the reaction mixture, whereby the target compound is synthesized.

The halogenated alkyl compound represented by the formula (VII) serves to efficiently esterify the carboxyl group of the compound (VI') with the group R so that the target compound of the formula (I) is prepared. Examples of the compound (VII) include those containing, as the group R, a tetrahydrofurylcarbonyloxymethyl group, tetrahydropyranylcarbonyloxymethyl group, 1,3-dioxolanylcarbonyloxymethyl group, 2-oxo-1,3-dioxolanylcarbonyloxymethyl group, 1,4-dioxanylcarbonyloxymethyl group or the like or its optically active isomer such as an (R)-2-tetrahydrofurylcarbonyloxymethyl group, (S)-2-tetrahydrofurylcarbonyloxymethyl group or (5-methyl-2-oxo-1,3-dioxolen-4-yl)methyl group and, as a halogen X, a chlorine, bromine or iodine atom.

No particular limitation is imposed on the alkali metal insofar as it forms a salt with the compound (VI'). Examples of the alkali metal include lithium, sodium and potassium. Examples of their hydroxides and salts include sodium hydroxide, potassium hydroxide, sodium bicarbonate, sodium carboxylate, potassium bicarbonate and potassium carbonate. Exemplary amine compounds include ammonia, triethylamine, and diisopropyl ethyl amine.

No particular limitation is imposed on the reaction solvent. Examples of the reaction solvent include aromatic hydrocarbons such as toluene and xylene, aliphatic hydrocarbons such as pentane and hexane, halogenated alkyls such as methylene chloride and chloroform, halogenated aryls such as chlorobenzenes, ketones such as acetone and methyl ethyl ketone, nitrites such as acetonitrile and propionitrile, amides such as dimethylformamide, sulfoxides such as dimethyl sulfoxide, ethers such as diethyl ether and tetrahydrofuran, and alcohols such as isopropanol and t-butanol. They can be used either singly or in combination.

The reaction may be carried out at room temperature or, when desired, under heating at a temperature below 80° C. The reaction time is generally 1–48 hours although it varies depending on the halogenated alkyl compound to be used.

As an alternative process for the preparation of the compound of this invention, the compound can also be synthesized by converting the compound of the formula (VI) into its chloromethyl or iodomethyl ester in accordance with the process proposed by B. Balzer et al. [J. Antibiotics, 33, 1183 (1980)] and then reacting it with a carboxylate salt represented by the following formula (VIII):

$R_5$—COOM (VIII)

wherein $R_5$ has the same meaning as Y and M is an alkali metal or an amino residuum.

This reaction is carried out at a temperature in the range of from −40° C. to room temperature, and is normally completed in 1–48 hours.

The penem compound (I) obtained as described above may be used as is but, in general, is purified, as needed, by a method such as column chromatography or recrystallization for use as a medicine.

For oral, parenteral or external administration, the compounds according to the present invention can be formulated as antibiotics in a manner known per se in the art.

Although the dosage of each penem derivative of the present invention varies depending on many factors, the typical daily dosage ranges from 50 mg to 3 g for standard adults with the administration of 100 mg to 2 g in divided portions being preferred. In general, the above dosage will be administered in the form of a dosage unit which contains an appropriate amount of the active ingredient and a suitable, physiologically-acceptable carrier or extender.

For oral administration, tablets or capsules can be used. They may contain—together with the active ingredient—an extender, e.g., lactose, glucose, sucrose, mannitol, sorbitol or cellulose, and a lubricant, e.g., talc, stearic acid or a stearate salt. Tablets may additionally contain a binder, for example, hydroxypropyl cellulose or starch.

The present invention will hereinafter be described more specifically by the following examples. It is however borne in mind that the present invention is not limited at all by these examples.

EXAMPLE 1

Chloromethyl (5R,6S)-6-[(R)-1-hydroxyethyl]-2-[(R)-2-tetrahydrofuryl]penem-3-carboxylate (Compound 6)

To the mixture of sodium (5R,6S)-6-[(R)-1-hydroxyethyl]-2-[(R)-2-tetrahydrofuryl]penem-3 -carboxylate 2.5 hydrate (Compound 1, 24.7 g), tetrabutylammonium sulfate (2.38 g) and potassium bicarbonate (21.0 g), water (70 ml) and methylene chloride (70 ml) were added. Into the resultant mixture, a solution of chloromethyl chlorosulfate (11.5 g) diluted in methylene chloride (280 ml) was added dropwise over about 10 minutes under ice cooling and stirring. After the reaction mixture was stirred for additional 2.5 hours at room temperature, the organic layer was collected and washed with water. The organic layer was dried and then concentrated. The residue so obtained was purified by passing it through a silica gel column. The title compound was obtained in the amount of 9.92 g.

EXAMPLE 2

Iodomethyl (5R,6S)-6-[(R)-1-hydroxyethyl]-2-[(R)-2-tetrahydrofuryl]penem-3-carboxylate (Compound 7)

The mixture of chloromethyl (5R,6S)-6-[(R)-1-hydroxyethyl]-2-[(R)-2-tetrahydrofuryl]penem-3-carboxylate (Compound 6, 334 mg), sodium iodide (225 mg) and acetone (2 ml) was stirred over night at room temperature, and the reaction mixture was concentrated. Ethyl acetate was added to the residue. The resultant solution was washed with water, dried, and then concentrated, whereby 359 mg of the title compound were obtained.

EXAMPLE 3

[5-(allyloxy)glutaryl]oxymethyl (5R,6S)-6-[(R)-1-hydroxyethyl]-2-[(R)-2-tetrahydrofuryl]penem-3-carboxylate (Compound 2)

The mixture of iodomethyl (5R,6S)-6-[(R)-1-hydroxyethyl]-2-[(R)-2-tetrahydrofuryl]penem-3-carboxylate (Compound 6, 3.4 g), sodium monoallylglutarate (3.83 g) and N,N-dimethylformamide (20 ml) was allowed to stand overnight at −20° C. The reaction mixture was then diluted with ethyl ether and washed with water. The organic layer was dried and then concentrated. The residue was purified by passing it through a silica gel column, whereby 0.553 g of the title compound was obtained.

EXAMPLE 4

(R)-2-tetrahydrofurylcarbonyloxymethyl (5R,6S)-6-[(R)-1-hydroxyethyl]-2-[(R)-2-tetrahydrofuryl]-penem-3-carboxylate (Compound 3)

The mixture of iodomethyl (5R,6S)-6-[(R)-1-hydroxyethyl]-2-[(R)-2-tetrahydrofuryl]penem-3-carboxylate (Compound 6, 3.4 g), (R)-tetrahydro-2-furoic acid sodium salt (1.38 g) and N,N-dimethylformamide (20 ml) was stirred for 2 hours at room temperature. The reaction mixture was diluted with ethyl ether and then washed with water. The organic layer was dried and concentrated. The residue was purified by passing it through a silica gel column, whereby 0.72 g of the title compound was obtained.

EXAMPLE 5

(S)-2-Tetrahydrofurylcarbonyloxymethyl (5R,6S)-6-[(R)-1-hydroxyethyl]-2-[(R)-2-tetrahydrofuryl]-penem-3-carboxylate (Compound 4)

The mixture of iodomethyl (5R,6S)-6-[(R)-1-hydroxyethyl]-2-[(R)-2-tetrahydrofuryl]penem-3-carboxylate (Compound 7, 3.4 g), (S)-tetrahydro-2-furoic acid sodium salt (1.38 g) and N,N-dimethylformamide (20 ml) was stirred for 2 hours at room temperature. The reaction mixture was diluted with ethyl ether, followed by washing with water. The organic layer was dried and then concentrated. The residue was purified by passing it through a silica gel column, whereby 0.92 g of the title compound was obtained.

EXAMPLE 6

(5-Methyl-2-oxo-1,3-dioxolen-4-yl)methyl (5R,6S)-6-[(R)-1-hydroxyethyl]-2-[(R)-2-tetrahydrofuryl] penem-3-carboxylate (Compound 5)

The mixture of sodium (5R,6S)-6-[(R)-1-hydroxyethyl]-2-[(R)-2-tetrahydrofuryl]penem-3-carboxylate 2.5 hydrate (Compound 1, 3.4 g), 4-iodomethyl-5-methyl-2-oxo-1,3-dioxolane (1.38 g) and N,N-dimethylformamide (20 ml) was stirred for 5 hours at room temperature. Water was added to the reaction mixture, and the resultant mixture was extracted with ethyl acetate. The ethyl acetate layer was washed with water, dried and then concentrated. The residue was purified by passing it through a silica gel column whereby 1.75 g of the title compound were obtained.

Physical properties of the compounds synthesized in Examples 2–7 are summarized in Table 1.

TABLE 1

| Comp'd No. | Compound | Appearance | $IR^{neat}$ (cm$^{-1}$) | NMR (CDCl$_3$) |
| --- | --- | --- | --- | --- |
| 2 | [[5-(allyloxy)glutaryl]oxy]-methyl (5R,6S)-6-[(R)-1-hydroxyethyl]-2-[[(R)-2-tetra-hydrofuryl]penem-3-carboxylate | Yellow oil | 3495, 2976 2879, 1790 1768, 1716 1324 | 1.34 (3H, d, J = 6.6 Hz), 1.72–1.86 (1H, m), 1.90–2.09 (3H, m), 2.34–2.53 (4H, m), 3.72 (1H, dd, J = 1.3 Hz, 6.6 Hz), 3.80–4.05 (2H, m), 4.18–4.27 (1H, m), 4.58 (2H, md, J = 5.3 Hz), 5.20–5.37 (3H, m), 5.51 (1H, d, J = 1.3 Hz), 5.80–5.98 (3H, m) |
| 3 | (R)-2-tetrahydrofurylcarbonyl-oxymethyl (5R,6S)-6-[(R)-1-hydroxyethyl]-2-[(R)-2-tetra-hydrofuryl]penem-3-carboxylate | Yellow oil | 3488, 2975 2877, 1786 1719, 1323 | 1.33 (3H, d, J = 6.0 Hz), 1.60–2.14 (6H, m), 2.17–2.31 (1H, m), 2.36–2.53 (1H, m), 3.71 (1H, dd, J = 1.3 Hz, 6.6 Hz), 3.82–4.09 (4H, m), 4.15–4.26 (1H, m), 4.47–4.55 (1H, m), 5.32 (1H, t, J = 7.3 Hz), 5.51 (1H, d, J = 1.3 Hz), 5.90 (2H, s) |
| 4 | (S)-2-tetrahydrofurylcarbonyl-oxymethyl (5R,6S)-6-[(R)-1-hydroxyethyl]-2-[(R)-2-tetra-hydrofuryl]penem-3-carboxylate | Yellow oil | 3466, 2975 2876, 1786 1719, 1323 | 1.34 (3H, d, J = 5.8 Hz), 1.52–2.16 (6H, m), 2.18–2.34 (1H, m), 2.38–2.52 (1H, m), 3.71 (1H, dd, J = 1.3 Hz, 6.6 Hz), 3.81–4.06 (4H, m), 4.15–4.28 (1H, m), 4.45–4.56 (1H, m), 5.31 (1H, t, J = 7.3 Hz), 5.50 (1H, d, J = 2 Hz), 5.88 (2H, dd, J = 5.9 Hz, 14.5 Hz) |
| 5 | (5-Methyl-2-oxo-1,3-dioxolen-4-yl)methyl (5R,6S)-6-[(R)-1-hydroxyethyl]-2-[(R)-2-tetra-hydrofuryl]penem-3-carboxylate | Pale yellow crystal | 3500, 1820 1785, 1706 1322 | 1.35 (3H, d, J = 6 Hz), 1.75–2.10 (3H, m), 2.20 (3H, s), 2.35–2.50 (1H, m), 3.72 (1H, d, J = 5 Hz), 3.80–4.05 (2H, m), 4.24 (1H, q, J = 5 Hz), 4.95 (2H, s), 5.31 (1H, t, J = 7 Hz), 5.50 (1H, s) |
| 6 | Chloromethyl (5R,6S)-6-[(R)-1-hydroxyethyl]-2-[(R)-2-tetra-hydrofuryl]penem-3-carboxylate | Pale yellow amorphous | | 1.36 (3H, d, J = 6.6 Hz), 1.38–2.09 (6H, m), 2.43–2.58 (1H, m), 3.73 (1H, dd, J = 2.0 Hz, 6.6 Hz), 3.83–4.04 (2H, m), 4.17–4.30 (1H, m), 5.28–5.37 (1H, m), 5.53 (1H, d, J = 1.3 Hz), 5.80 (2H, dd, J = 5.9 Hz, 23.8 Hz) |
| 7 | Iodomethyl (5R,6S)-6-[(R)-1-hydroxyethyl]-2-[(R)-2-tetra-hydrofuryl]penem-3-carboxylate | Yellow crystal | | 1.36 (3H, d, J = 6.6 Hz), 1.73–2.12 (3H, m), 2.45–2.60 (1H, m), 3.73 (1H, dd, J = 1.3 Hz, 5.9 Hz), 3.81–4.04 (2H, m), m), 4.18–4.31 (1H, m), 5.33 (1H, t, J = 7.3 Hz), 5.52 (1H, d, J = 1.3 Hz), 6.01 (2H, s) |

EXAMPLE 7

The bioavailability of certain compounds (I) of the present invention was tested relying upon their recovery rates in urine.

Each test compound (30 μmole/kg) was orally administered to SD strain rats (three male rats per group). Urine was collected over 6 hours from the administration, and the recovery rate of the corresponding compound present in the urine was determined by bioassay. The results are shown below.

TABLE 2

| Comp'd No. | R in the compound (I) | Urinary recovery (%) | Ratio |
|---|---|---|---|
| 1 | Na | 4.38 | 1 (Control) |
| 2 | $-CH_2OCO(CH_2)_3COOCH_2CHCH_2$ | 7.53 | 1.7 |
| 3 | 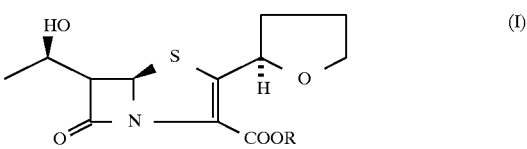 | 10.90 | 2.5 |
| 4 | | 11.57 | 2.6 |
| 5 | | 22.27 | 5.1 |

As is apparent from the results, the compounds (I) of the present invention showed the higher urinaly recovery rate, in other words, a higher bioavailability compared with the penem compound (VI).

The compounds according to the present invention can be used not only for men but also for animals.

In each of the following preparation examples, the active ingredient may be, for example, Compound 5 or an equivalent amount of any one of the other compounds of the present invention.

PREPARATION EXAMPLE 1

| | Capsules | |
|---|---|---|
| Ingredient No. | Ingredient | mg/capsule |
| 1 | Invention compound | 150 |
| 2 | Lactose | 20 |
| 3 | Magnesium stearate | 4 |
| | (Total) | 174 mg |

(Production procedures)

Ingredients 1 and 2 were combined together in a suitable mixer, to which Ingredient 3 was added, followed by further mixing. The resultant mixture was filled by a capsule filling machine.

PREPARATION 2

| | Tablets | |
|---|---|---|
| Ingredient No. | Ingredient | mg/tablet |
| 1 | Invention compound | 150 |
| 2 | Crystalline cellulose | 50 |
| 3 | Calcium carboxymethylcellulose | 10 |
| 4 | Magnesium stearate | 4 |
| | (Total) | 214 mg |

(Production procedures)

Ingredients 1–3 were combined together in a suitable mixer, to which Ingredient 4 was added, followed by mixing for additional several minutes. The resultant mixture was compressed into tablet of a predetermined size and weight by a tablet machine.

INDUSTRIAL APPLICABILITY

As has been described above, the compounds of the present invention exhibit an excellent bioavailability so that they can be advantageously used as oral antibiotics.

We claim:

1. A process for the preparation of a penem compound represented by formula (I):

wherein R represents a group of the formula $-CH_2-Z$ in which Z is a 5-substituted 2-oxo-1,3-dioxolen-4-yl group, said 5-substituent being a $C_1-C_6$ alkyl group, a $C_6-C_{10}$ aryl group, a $C_7-C_{11}$ aralkyl group, or said 5-substituent is substituted by one or more substituents selected from the group consisting of $C_1-C_6$ alkyl, $C_6-C_{10}$ aryl, $C_7-C_{11}$ aralkyl, hydroxyl, $C_1-C_6$ alkoxyl and halogen, which comprises reacting a halogenated alkyl compound (VII):

RX (VII)

in which X represents a halogen atom, and R has the same meaning as defined above, with a penem compound (VI'):

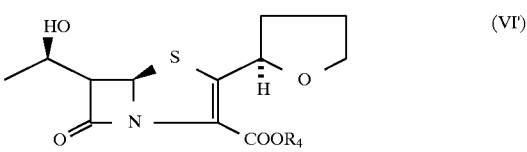

in which $R_4$ represents a hydrogen or alkali metal or an amino residuum.

2. The process according to claim 1, wherein R represents a (5-methyl-2-oxo-1,3-dioxolen-4-yl)methyl group.

3. The process according to claim 1, wherein the penem compound is (5-methyl-2-oxo-1,3-dioxolen-4-yl)methyl (5R, 6S)-6-[(R)-1-hydroxyethyl]-2-[(R)-2-tetrahydrofuryl]-penem-3-carboxylate.

4. A method of treating animals or humans in need of an antibiotic comprising administering to such animals or humans effective amount of a penem compound represented by formula (1):

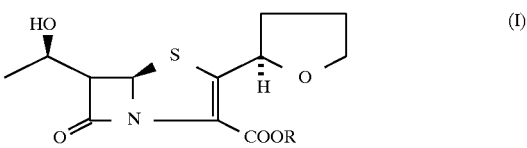

wherein R represents a group of the formula $-CH_2-Z$ in which Z is a 5-substituted 2-oxo-1,3-dioxolen-4-yl group, said 5-substituent being a $C_1-C_6$ alkyl group, a $C_6-C_{10}$ aryl group, a $C_7-C_{11}$ aralkyl group, or said 5-substituent is substituted by one or more substituents selected from the group consisting of $C_1-C_6$ alkyl, $C_6-C_{10}$ aryl, $C_7-C_{11}$ aralkyl, hydroxyl, $C_1-C_6$ alkoxyl and halogen.

5. The method according to claim 1, wherein R represents a (5-methyl-2-oxo-1,3-dioxolen-4-yl)methyl group.

6. The method according to claim 1, wherein the penem compound is (5-methyl-2-oxo-1,3-dioxolen-4-yl)methyl (5R, 6S)-6-[(R)-1-hydroxyethyl]-2-[(R)-2-tetrahydrofuryl]-penem-3-carboxylate.

7. The method according to claim 1, wherein the penem compound is orally administered.

* * * * *